United States Patent [19]

Patel et al.

[11] Patent Number: 6,149,914
[45] Date of Patent: Nov. 21, 2000

[54] ASTHMA TREATMENT

[76] Inventors: Jitendra Rambhai Patel, Rughnathji Pole, Ahmedabadi Bazar, Nadiad 387 001, India; Devendra Rambhai Patel, 78-09 24th Ave., Jackson Heights, N.Y. 11370

[21] Appl. No.: 09/351,449

[22] Filed: Jul. 12, 1999

[51] Int. Cl.[7] .......................... A61K 35/78; A61K 47/00
[52] U.S. Cl. ........................................ 424/195.1; 434/439
[58] Field of Search ................................. 424/195.1, 439

[56] References Cited

U.S. PATENT DOCUMENTS

| | | |
|---|---|---|
| 4,338,931 | 7/1982 | Cavazza . |
| 4,446,130 | 5/1984 | Hachiya et al. . |
| 5,301,666 | 4/1994 | Lerk et al. . |
| 5,352,694 | 10/1994 | Cuthbert . |
| 5,665,359 | 9/1997 | Ho et al. . |
| 5,823,183 | 10/1998 | Casper et al. . |

*Primary Examiner*—Francisco Prats
*Assistant Examiner*—Susan D. Coe
*Attorney, Agent, or Firm*—Michael I. Knoll

[57] ABSTRACT

A composition (10) for treating the symptoms of bronchial asthma in a human requiring such treatment includes an orally effective amount of dried (28), powdered (30) interior bark from the sacred fig tree of India, *Ficus religiosa* (12). The composition (10) is admixed with a foodstuff such a rice pudding (14), for ingestion by the patient.

13 Claims, 2 Drawing Sheets

ASTHMA TREATMENT

BACKGROUND OF THE INVENTION

1. Field of the Invention

The instant invention relates generally to compositions for treating the symptoms of asthma in a human patient, and specifically to an orally administered composition derived from natural sources for treating the symptoms of bronchial asthma.

Bronchial asthma is a relatively common lung disorder characterized by periodic attacks of wheezing alternating with periods of relatively normal breathing. While bronchial asthma is usually intrinsic (no cause can be demonstrated), it is occasionally caused by a specific allergy (e.g., pollen, mold, dander, dust). Although most individuals with asthma will have some positive allergy tests, the allergy is not necessarily the cause of the asthma symptoms.

Symptoms can occur spontaneously or can be triggered by respiratory infections, exercise, cold air, tobacco smoke or other pollutants, or by allergies to foods, drugs or other irritants, such as chemicals, dust mites, feathers, food additives, fumes, mold, animal dander, and the like. Other things can also trigger asthmatic episodes: anxiety, fear, laughing, stress or anxiety, low blood sugar, adrenal disorders, temperature changes, extremes of dryness or humidity, or respiratory infections. The muscles of the bronchial tree become tight and the lining of the air passages become swollen, reducing airflow and producing a wheezing sound. Mucus production is generally increased.

With regard to the typical symptoms, wheezing usually begins suddenly, is often worse at night or in the early morning, is commonly aggravated by exposure to cold air, sudden exercise or both, and sometimes resolves itself spontaneously. In many patients, wheezing is accompanied by a cough with sputum (phlegm) production containing mucus (mucoid sputum). In severe cases, there may be extreme difficulty breathing, a bluish color to the lips and face, severe anxiety which can result in a dangerous positive feedback effect, rapid pulse and/or sweating.

Typically, the afflicted individual breathes relatively normally most of the time, but will have periodic attacks of wheezing. Asthma attacks can last minutes to days, and can become dangerous if the airflow becomes severely restricted. Asthma affects approximately 5 percent of the overall population, but the incidence is higher, about 1 in 10, in children. Asthma can develop at any age, but some children seem to outgrow the illness. Risk factors include self or family history of eczema, allergies or a family history of asthma.

Treatment generally takes a two-pronged approach consisting of 1) avoiding known allergens and 2) controlling symptoms through medication.

A variety of medications for treatment of asthma are available and include anti-inflammatory medications such as inhaled corticosteroids, oral or intravenous corticosteroids, and non-steroidal compositions such as nedocromil sodium. Also commonly prescribed are bronchodilators, both inhaled and orally administered, cromolyn sodium, which is used to prevent attacks, not for treatment during an attack, and aminophylline or theophylline.

People with mild asthma (infrequent attacks) are generally prescribed inhalers for use on an as-needed basis. Those with significant asthma (symptoms occur once per week or more) are generally treated with anti-inflammatory medications, such as inhaled corticosteroids, and then with bronchodilators for acute attacks. Severe acute asthma, left untreated, is known to require hospitalization, oxygen, and intravenous medications.

2. Description of the Related Art

Compositions for treating asthma are known in the art and generally comprise a pharmaceutical compound which is administered either via inhalation or oral ingestion, usually in tablet form. For example, U.S. Pat. No. 4,338,931 (Cavazza, C., Jul. 13, 1982), U.S. Pat. No. 5,301,666 (Lerk, C., et al., Apr. 12, 1994) and U.S. Pat. No. 5,823,183 (Casper, R. A., et al., Oct. 20, 1998) each disclose a method of administering a dry powder medicament directly to the lungs via inhalation.

U.S. Pat. No. 5,352,694 (Cuthbert, M. W., Oct. 4, 1994) discloses an orally administered pharmaceutical compound which is a leukotriene antagonist useful in treating conditions such as asthma.

SUMMARY OF THE INVENTION

The present invention is concerned with a composition for for treating the symptoms of asthma in a human patient, and specifically to an orally administered composition derived from natural sources for treating the symptoms of bronchial asthma.

A primary object of the present invention is to provide a method and composition for treating the symptoms of bronchial asthma which includes, as the active component, a natural material derived from the bark of the aswatha (*Ficus religiosa*) tree.

Another object of the present invention is to provide a method and composition for treating the symptoms of bronchial asthma which can provide lasting relief from such symptoms.

An additional object of the present invention is to provide an ingestible composition for treating bronchial asthma which is palatable and nutritious.

A further object of the present invention is to provide an ingestible composition for treating bronchial asthma which is easy to prepare, economical to manufacture and safe and convenient to use.

The foregoing and other objects, advantages and characterizing features will become apparent from the following description of certain illustrative embodiments of the invention.

The novel features which are considered characteristic for the invention are set forth in the appended claims. The invention itself, however, both as to its construction and its method of operation, together with additional objects and advantages thereof, will be best understood from the following description of the specific embodiments when read and understood in connection with the accompanying drawings. Attention is called to the fact, however, that the drawings are illustrative only, and that changes may be made in the specific construction illustrated and described within the scope of the appended claims.

BRIEF DESCRIPTION OF THE DRAWING FIGURES

Various other objects, features and attendant advantages of the present invention will become more fully appreciated as the same becomes better understood when considered in conjunction with the accompanying drawings, in which like reference characters designate the same or similar parts throughout the several views.

DESCRIPTION OF THE PREFERRED EMBODIMENTS

Figure 1:
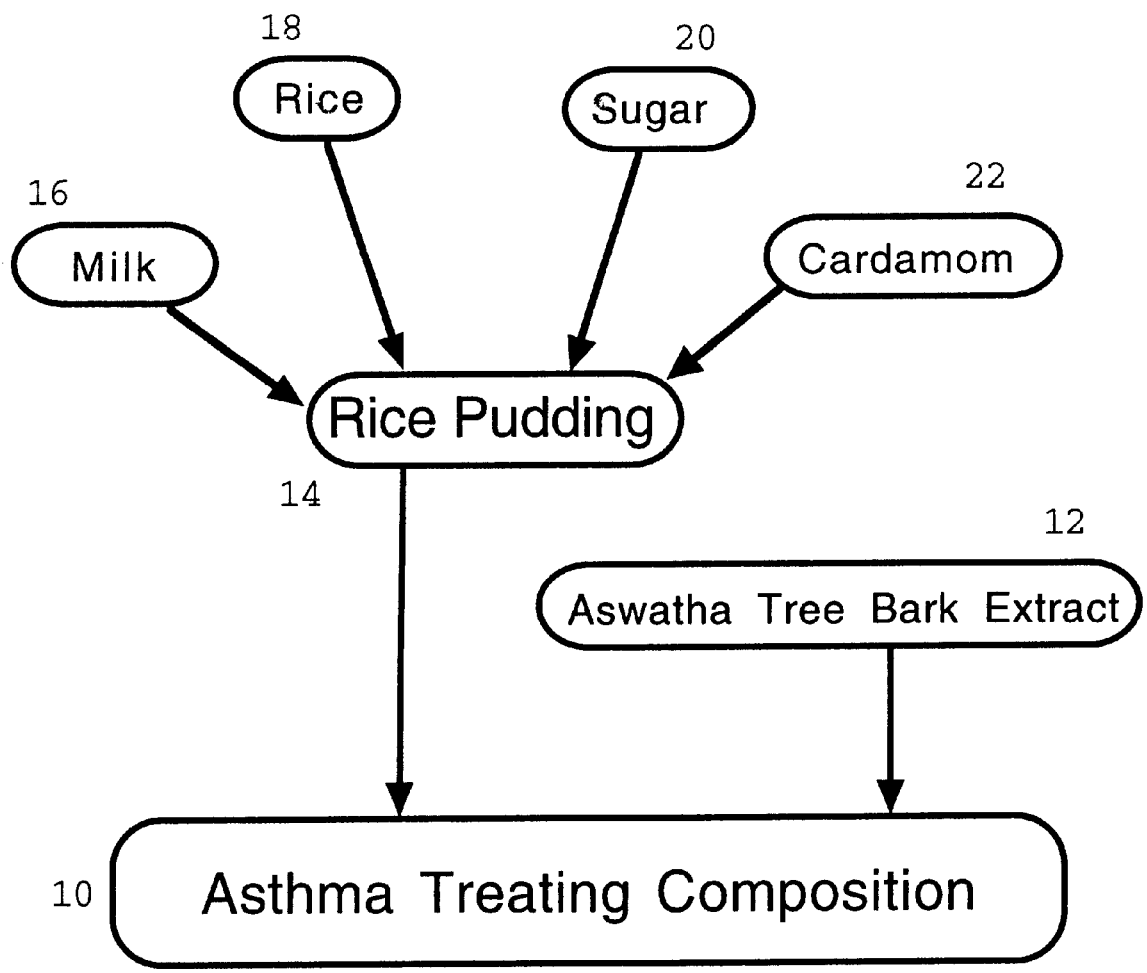
FIG. 1 is a graphic depiction of the various components which find utility in the composition of the present invention.

Turning now descriptively to the drawings, in which similar reference characters denote similar elements throughout the several views, the Figures illustrate a composition for treating the symptoms of bronchial asthma in a human patient. With regard to the reference numerals used, the following numbering is used throughout the various drawing figures.

Figure 2:
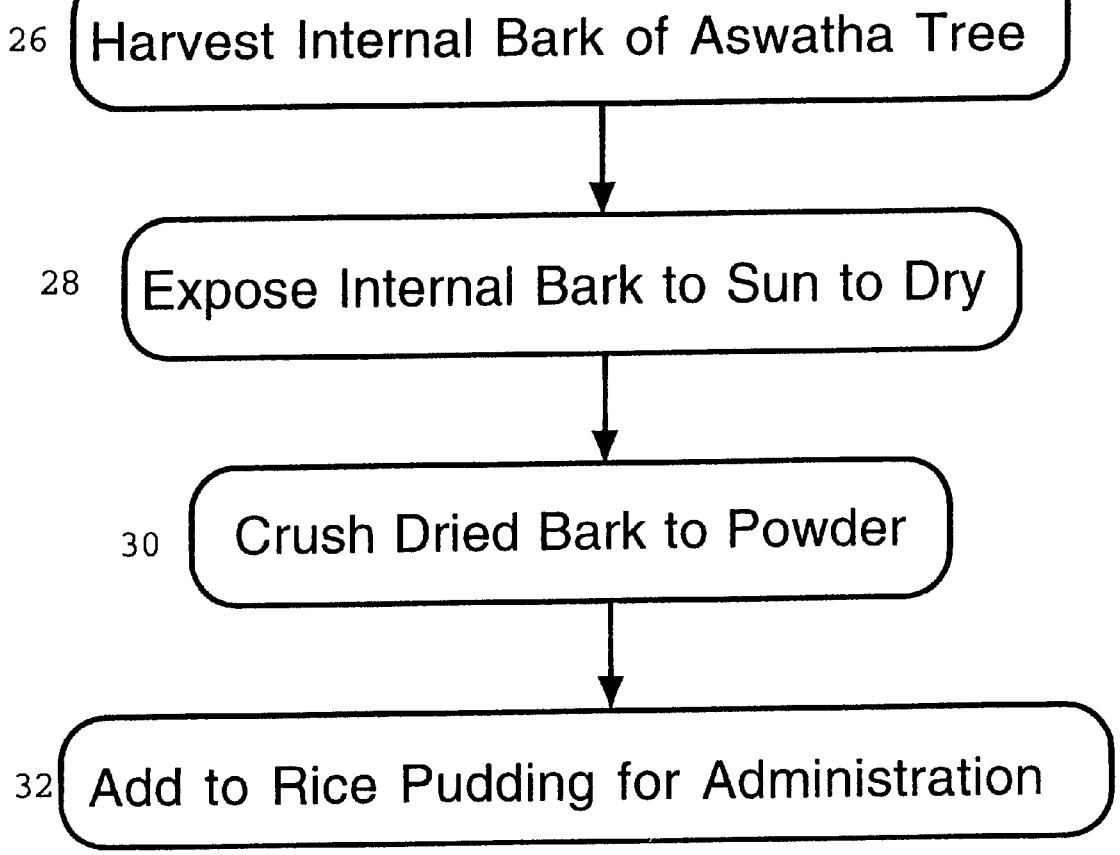
FIG. 2 is a flowchart illustrating the basic steps in preparing the active component and its incorporation into the asthma-treating composition of the invention.

10 composition for treating asthma
12 the active ingredient in 10, Aswatha tree bark extract
14 the food carrier of 10, rice pudding
16 milk component of 14
18 rice component of 14
20 sugar component of 14
22 cardamom component of 14
24 process for preparing 10
26 harvesting of Aswatha tree bark
28 exposing bark to sun in order to dehydrate
30 crushing dehydrated bark to a powdered form
32 incorporating crushed, dried bark into rice pudding FIGS. 1 and 2 illustrate a composition 10 and method for preparing a composition 24 for treating the symptoms of bronchial asthma in a human patient. The active ingredient in the composition of the invention is derived from the interior bark of the Indian Fig tree 12, known regionally as Aswatha, and with the latin name *Ficus religiosa*. It has been discovered that the internal bark of the tree, when prepared and administered orally as set forth herein, can provide long lasting relief from the symptoms of bronchial asthma in human patients afflicted with bronchial asthma. It has been determined in particular that a particularly suitable vehicle for oral administration of the material is rice pudding 14, a traditional dessert dish in India. When admixed 32 with rice pudding 14, the prepared extract from the Aswatha tree bark 12 can be palatably administered and readily absorbed.

To prepare 24 the extract 12, first the internal bark is harvested 26 from a mature *Ficus religiosa* tree, preferably from the portion of the tree nearest the bottom of the trunk, and the harvested bark is allowed to dehydrate 28. while dehydration may be accomplished via modern methods including vacuum dehydration, heating chambers, sonic dehydration and the like, it is preferred to dry the bark slowly utilizing sunlight 28 and ambient conditions, according to ancient traditional drying methods. For example, the harvested bark has been placed in direct morning sun for about two hours each day, then was left in shade for the remainder of the day. After several days, the bark was suitably dehydrated and ready for further processing. While it can be appreciated that dehydration by any means results in a suitably dehydrated material, the traditional method, which includes direct exposure to the rays of the sun and ambient conditions, may produce a materially different product, for example by virtue of the exposure of the bark to UV (ultraviolet) radiation. All dehydrated forms of the bark of the tree are within the scope of the present invention.

After dehydration, the bark is crushed 30 by conventional means, for example in a mill, to a finely powdered form which can be incorporated 32 directly into the composition 10 of the present invention.

With regard to administration, it can be readily appreciated that the powdered bark 12 may be readily incorporated into capsules, tablets and the like, including the use of pharmaceutically acceptable carriers if desired. Preferably, the powdered bark is incorporated into foodstuffs for direct ingestion by the patient. A particularly suitable foodstuff is rice pudding 14, a traditional Indian dessert made from milk 16, rice 18, sugar 20 and cardamom 22. The powdered bark 12 mixes well in the rice pudding 14, is readily palatable and easily absorbed.

It has been found that a single administration of the composition of the invention can relieve the symptoms of asthma for a long period of time, such that asthmatic episodes happen rarely or not at all for some patients. An effective amount of the powdered is generally from about 1 to about 20 grams per dosage, preferably from about 3 to about 12 grams, and most preferably about 6 grams.

EXAMPLE

The internal bark of a *Ficus religiosa* (about ½ inch thick) tree was collected from the bottom of the tree. It was placed in direct sunlight for about 2 hours, then was placed in the shade. After several days, the bark was dried sufficiently to be ground to a very fine powder in a mill. The powdered bark was added to rice pudding prepared as follows.

To 150 grams of milk was added 1 teaspoon of sugar. The mixture was heated until the milk thickened. At this point ⅓ tablespoon of rice and 2 cardamom seeds were added to the mixture. Heat was removed and the mixture was allowed to cool for 1 to 2 hours. After cooling, 6 grams of the powdered bark was added and the mixture was stirred, then allowed to stand for about 4 hours. The mixture is then administered to the patient for oral ingestion. With this procedure, about 90 to 95% of patients exhibit marked improvement which persists over a period of many weeks to months.

It will be understood that each of the elements described above, or two or more together, may also find a useful application in other types of applications differing from the type described above. These include, for example, diseases or conditions for which inflammation or pain has been implicated, for example, arthritis, fever, eclampsia and the like.

While the invention has been illustrated and described as embodied in a method and composition for treating the symptom of bronchial asthma, it is not intended to be limited to the details shown, since it will be understood that various omissions, modifications, substitutions and changes in the forms and details of the formulation illustrated and in its operation can be made by those skilled in the art without departing in any way from the spirit and scope of the present invention.

Without further analysis, the foregoing will so fully reveal the gist of the present invention that others can, by applying current knowledge, readily adapt it for various applications without omitting features that, from the standpoint of prior art, fairly constitute essential characteristics of this invention.

What is claimed as new and desired to be protected by Letters Patent is set forth in the appended claims:

1. A composition for treating the symptoms of bronchial asthma comprising an orally effective amount of dried, powdered interior bark from *Ficus religiosa* admixed with a rice pudding comprising milk, sugar, rice and cardamom.

2. A composition as recited in claim 1, wherein said orally effective amount is between about 1 and about 20 grams.

3. A composition as recited in claim 2, wherein said orally effective amount is between about 3 and about 12 grams.

4. A composition as recited in claim 3, wherein said orally effective amount is about 6 grams.

5. A composition as recited in claim 1, wherein said dried, powdered bark is dried under conditions including exposure to ultraviolet light.

6. A composition as recited in claim 5, wherein said dried, powdered bark is dried under conditions including exposure to direct sunlight.

7. A method of treating symptoms of bronchial asthma in a human patient requiring such treatment, comprising administering to such person a composition as defined in claim 1.

8. A method of treating symptoms of bronchial asthma in a human patient requiring such treatment, comprising administering to such person a composition as defined in claim 2.

9. A method of treating symptoms of bronchial asthma in a human patient requiring such treatment, comprising administering to such person a composition as defined in claim 6.

10. The method of preparing a composition for treating the symptoms of bronchial asthma comprising the steps of:

a) harvesting internal bark from a mature Ficus religiosa tree;

b) allowing the harvested bark to dehydrate by exposing the bark to sunlight containing UV at ambient conditions for about two hours followed by leaving the bark in the shade until dehydrated;

c) crushing the bark to a powdered form;

d) preparing a rice pudding from milk, sugar, rice and cardamom seeds;

e) adding the powdered bark to the rice pudding; and f) stirring the mixture and allowing the mixture to stand for about four hours before the mixture is administered to a patient.

11. The method of claim 10 in which the *Ficus religiosa* is present in the amount of between 1 and about 20 grams for a single dose.

12. The method of claim 11 in which the *Ficus religiosa* is present in the amount of between 3 and about 12 grams for a single dose.

13. The method of claim 12 in which the *Ficus religiosa* is present in the amount of about 6 grams for a single dose.

* * * * *